United States Patent
Kaur (10) Patent No.: US 11,484,206 B2
(45) Date of Patent: Nov. 1, 2022

(54) IMPLANTABLE DEVICE FOR DETECTING LIGHT CORRELATING TO VESSEL

(71) Applicant: ENT. SERVICES DEVELOPMENT CORPORATION LP, Houston, TX (US)

(72) Inventor: Satwant Kaur, Mountain View, CA (US)

(73) Assignee: ENT. SERVICES DEVELOPMENT CORPORATION LP, Houston, TX (US)

( * ) Notice: Subject to any disclaimer, the term of this patent is extended or adjusted under 35 U.S.C. 154(b) by 367 days.

(21) Appl. No.: 15/510,840

(22) PCT Filed: Nov. 25, 2014

(86) PCT No.: PCT/US2014/067389
§ 371 (c)(1),
(2) Date: Mar. 13, 2017

(87) PCT Pub. No.: WO2016/085475
PCT Pub. Date: Jun. 2, 2016

(65) Prior Publication Data
US 2017/0273561 A1    Sep. 28, 2017

(51) Int. Cl.
*A61B 5/00*        (2006.01)
*A61B 5/026*       (2006.01)
*A61B 5/107*       (2006.01)
*A61B 5/07*        (2006.01)
(Continued)

(52) U.S. Cl.
CPC .......... *A61B 5/0031* (2013.01); *A61B 5/0017* (2013.01); *A61B 5/0261* (2013.01); *A61B 5/07* (2013.01); *A61B 5/686* (2013.01); *A61F 2/06* (2013.01); *A61B 5/107* (2013.01);
(Continued)

(58) Field of Classification Search
CPC ... A61B 5/0031; A61B 5/0017; A61B 5/0261; A61B 5/07; A61B 5/686; A61B 5/107; A61B 6/12; A61B 2560/0219; A61B 2560/0223; A61F 2/06
See application file for complete search history.

(56) References Cited

U.S. PATENT DOCUMENTS

| 5,305,745 A | 4/1994 | Zacputo |
| 6,106,477 A | 8/2000 | Miesel et al. |

(Continued)

FOREIGN PATENT DOCUMENTS

| WO | WO-2005120335 | 12/2005 |
| WO | WO-2009008932 | 1/2009 |

OTHER PUBLICATIONS

International Search Report and Written Opinion dated Aug. 21, 2015, PCT Patent Application No. PCT/US2014/067389, filed Nov. 25, 2014, Korean Intellectual Property Office.
(Continued)

*Primary Examiner* — Navin Natnithithadha
(74) *Attorney, Agent, or Firm* — Polsinelli PC (57) ABSTRACT

Example implementations relate to an implantable device that can accommodate a vessel of a living body and can detect light transmitted across the vessel. The implantable device transmits a wireless transmitter signal corresponding to the intensity of the detected light. The intensity of the detected light correlates to patency of the vessel.

6 Claims, 10 Drawing Sheets

(51) Int. Cl.
*A61B 6/12* (2006.01)
*A61F 2/06* (2013.01)

(52) U.S. Cl.
CPC ......... *A61B 6/12* (2013.01); *A61B 2560/0219* (2013.01); *A61B 2560/0223* (2013.01)

(56) References Cited

U.S. PATENT DOCUMENTS

| | | | |
|---|---|---|---|
| 6,731,967 B1* | 5/2004 | Turcott | A61B 5/0261 600/407 |
| 8,267,954 B2 | 9/2012 | Decant et al. | |
| 8,290,557 B2 | 10/2012 | Davis et al. | |
| 2002/0155425 A1* | 10/2002 | Han | A61B 5/14532 435/4 |
| 2006/0110283 A1 | 5/2006 | Fish | |
| 2008/0221464 A1* | 9/2008 | Al-Ali | A61B 5/0261 600/500 |
| 2009/0157058 A1* | 6/2009 | Ferren | A61B 5/6876 604/891.1 |
| 2009/0192534 A1* | 7/2009 | Ortiz | A61B 5/0028 606/157 |
| 2010/0016733 A1* | 1/2010 | Smith | A61B 5/02007 600/483 |
| 2011/0208067 A1 | 8/2011 | Edman et al. | |
| 2011/0218448 A1* | 9/2011 | Buntic | A61B 5/0261 600/504 |
| 2013/0030307 A1* | 1/2013 | Rajan | A61B 5/0261 600/479 |
| 2013/0079657 A1* | 3/2013 | Ochs | A61B 5/7235 600/529 |
| 2013/0116575 A1* | 5/2013 | Mickle | A61B 5/7415 600/479 |
| 2013/0123600 A1* | 5/2013 | Tcheng | A61B 5/0478 600/378 |
| 2014/0081154 A1* | 3/2014 | Toth | A61B 5/6862 600/479 |
| 2014/0107493 A1* | 4/2014 | Yuen | A61B 5/6898 600/473 |
| 2016/0022157 A1* | 1/2016 | Melker | A61B 5/02108 600/407 |

OTHER PUBLICATIONS

Osman Salem et al ~ Anomaly Detection in Medical Wireless Sensor Networks using SVM and Linear Regression Models ~ Int'l Jrn of E-Health & Medical Communications Jan./Mar. 2014 ~ 4 pages.

* cited by examiner

IMPLANTABLE DEVICE FOR DETECTING LIGHT CORRELATING TO VESSEL

CLAIM FOR PRIORITY

The present application is a national stage filing under 35 U.S.C. § 371 of PCT application number PCT/US2014/067389, having an international filing date of Nov. 25, 2014, the disclosure of which is hereby incorporated by reference in its entirety.

BACKGROUND

Vascular occlusion can reduce blood vessel patency and blood flow in a living body. Vascular occlusion can result from, among other causes, atherosclerosis, thrombogenesis, and embolisms. Complications arising from vascular occlusions can include ischemia, embolism, and death.

BRIEF DESCRIPTION OF THE DRAWINGS

Various examples will be described below with reference to the following figures. Different ones of the figures may have at least some reference numerals that are the same in order to identify similar, though perhaps not identical, components. For the sake of brevity, a detailed description of each such component having a previously described function may not be provided below with respect to other figures in which they appear.

DETAILED DESCRIPTION

"Vessel patency," as referred to herein, should be understood to refer to the degree of openness of a vessel in a living body. Vessel patency can be reduced in a living body by many causes, including the build-up of atherosclerotic plaque in a vessel or the formation of a thrombus (also known as a blood clot) in a vessel. Reduced blood flow accompanying a reduction in vessel patency can lead to ischemia. Furthermore, a thrombus can dislodge from a vessel wall and cause a blockage elsewhere in the circulatory system, thus causing further complications, such as pulmonary embolism, cerebral stroke, myocardial infarction, and the like. For example, a heart transplant procedure includes one or more anastomoses of the left atrium, right atrium, superior vena cava, inferior vena cava, pulmonary artery, and aorta, in order to connect a donor heart to a recipient circulatory system. Such anastomoses may be sites for thrombus formation. Post-operative monitoring includes periodic catheter-based imaging and/or laboratory blood tests, which may not be performed frequently enough to detect post-operative thrombogenesis. Accordingly, an implantable device for monitoring vessel patency may be useful for reducing post-operative complications.

Figure 1:
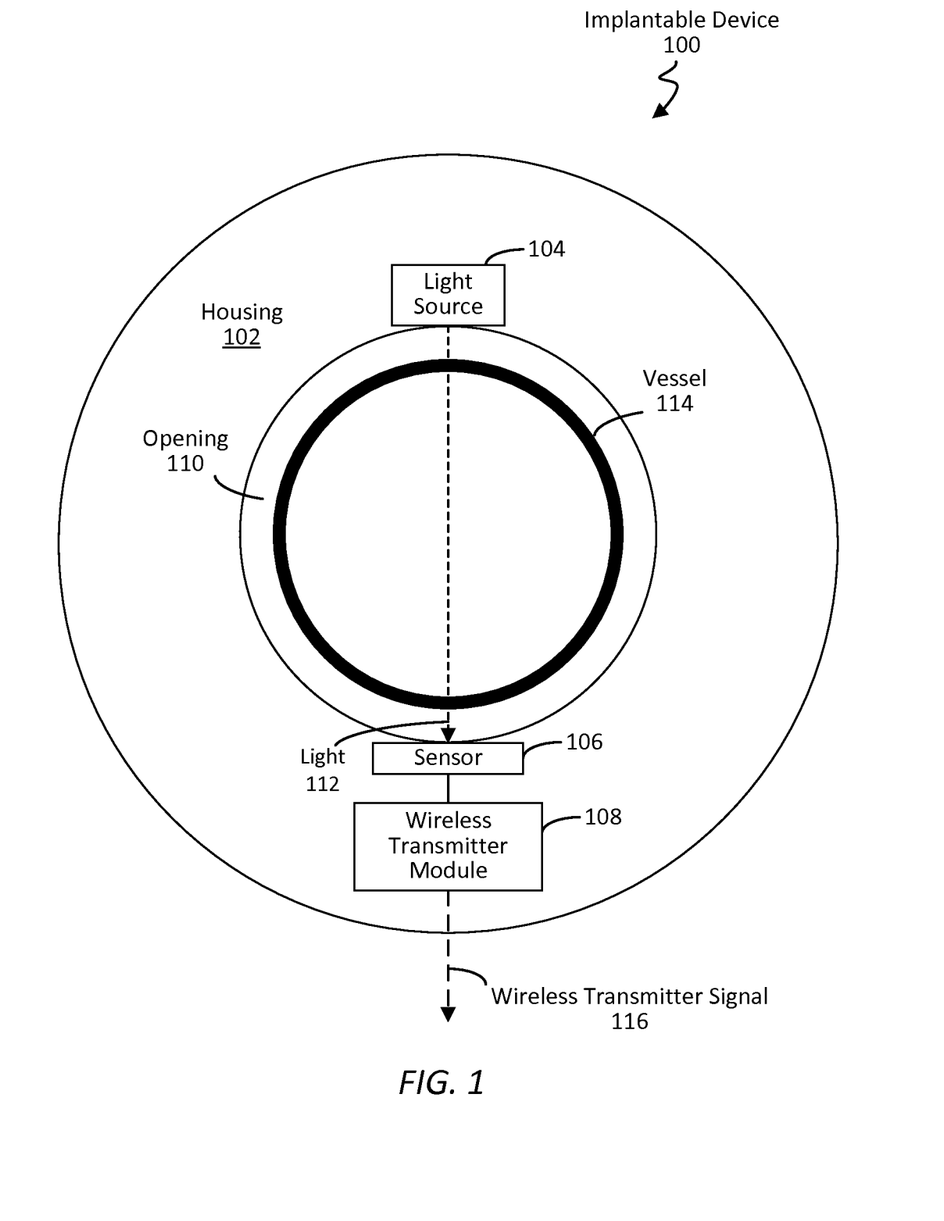
FIG. 1 is a schematic diagram of an implantable device according to an example implementation.

Referring now to the figures, FIG. 1 is a schematic diagram of an implantable device 100 according to an example implementation that can include a housing 102, a light source 104, a sensor 106, and a wireless transmitter module 108. A module, as referred to herein, can include a set of instructions encoded on a machine-readable storage medium and executable by a processor. Additionally or alternatively, a module may include a hardware device comprising electronic circuitry for implementing functionality described herein.

The housing 102 can include an opening 110 for accommodating a vessel 114 of a living body. In some example implementations, the housing 102 can be constructed of a biocompatible material, such as, for example, titanium, ceramic, silicone, and/or other polymers. In some example implementations, the opening 110 can have a size substantially similar to the vessel 114, such that the vessel 114 fills all or substantially all of the opening 110. It should be understood that the vessel 114 is illustrated in the figures as being smaller than the opening 110 for the purposes of legibility.

The light source 104 can be embedded into the housing 102, and can emit light. In some example implementations, the light source 104 can be a light emitting diode (LED). In some example implementations, the light source 104 can emit light having a wavelength in a range from approximately 400 nm to approximately 700 nm (also known as the visible spectrum). In other example implementations, the light source 104 can emit light having a wavelength in a range from approximately 700 nm to approximately 1400 nm (also known as near infrared light), and more particularly, around 900 nm (e.g. 900 nm ±100 nm). As referred to herein, the term "embedded" should be understood to include implementations where the embedded component is encapsulated, as well as implementations where the embedded component is not encapsulated (e.g., the component can be exposed or can protrude).

The sensor 106 can be embedded into the housing 102 and can detect light 112 transmitted from the light source 104 across the opening 110. For example, when the vessel 114 is accommodated in the opening 110, the sensor 106 can detect light 112 from the light source 104 transmitted across (or in other words, passing through) the vessel 114 accommodated in the opening 110.

In some example implementations, the sensor 106 can be a photodetector (e.g., a photodiode) that converts light 112 arriving at the sensor 106 into a sensor signal, such as an electric current, having a value that is proportional (e.g., by linear proportionality, logarithmic proportionality, or the like) to the intensity of the light 112 arriving at the sensor 106. For example, a higher intensity of light 112 can be converted to a greater electric current, and a lower intensity of light 112 can be converted to a lower electric current. In some example implementations, the sensor 106 can be a silicon photodiode that is sensitive to light in the wavelength range from approximately 400 nm to 1100 nm, with a peak sensitivity around 900 nm.

Figure 2A:
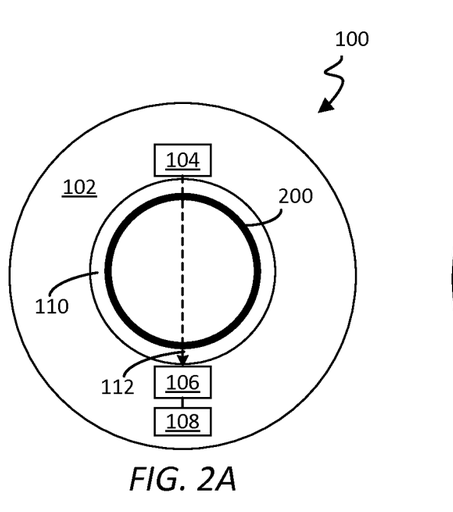
FIG. 2A is a schematic diagram of the example implantable device of FIG. 1 accommodating an unoccluded vessel.
Figure 2B:
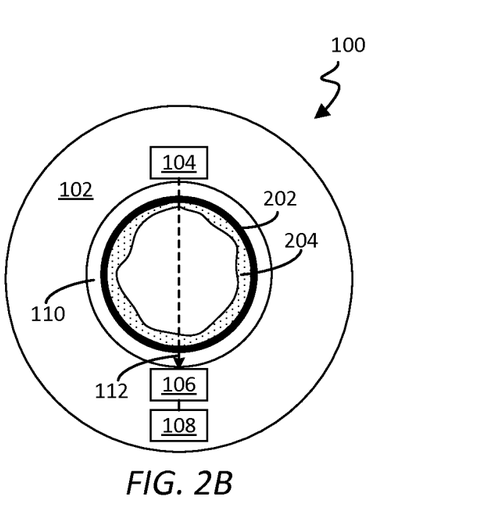
FIG. 2B is a schematic diagram of the example implantable device of FIG. 1 accommodating a partially occluded vessel.
Figure 2C:
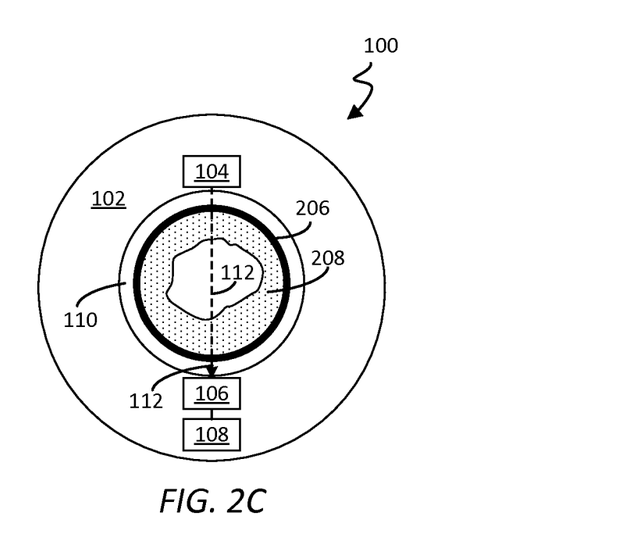
FIG. 2C is a schematic diagram of the example implantable device of FIG. 1 accommodating a vessel that is more occluded than the vessel illustrated in FIG. 2B.

An intensity of light 112 detected by the sensor 106 can correlate to (in other words, correspond to, vary with, or be a function of) patency of the vessel 114 accommodated in the opening 110. An example of the sensitivity of light 112 to vessel patency will now be illustrated with reference to FIGS. 2A-2C. FIG. 2A illustrates a vessel 200 that is not occluded and has high patency, FIG. 2B illustrates a vessel 202 that is partially occluded by occlusive material 204, and FIG. 2C illustrates a vessel 206 that is partially occluded by occlusive material 208. The vessel 206 of FIG. 2C is more occluded than (has lower patency than) the vessel 202 of FIG. 2B, and the vessel 202 of FIG. 2B is more occluded than (has lower patency than) the vessel 200 of FIG. 2A. Occluding material that reduces blood flow through the vessel (e.g., a thrombus, an atherosclerotic plaque, an onset of blood coagulation, and the like) can have a greater light attenuation coefficient than blood. Accordingly, decreasing vessel patency due to increasing amounts of occluding material in the vessel can correlate with a decreasing intensity of light 112 transmitted across the vessel and detected by the sensor 106. Accordingly, the sensor 106 may detect a lower intensity of light 112 transmitted across the vessel 202 of FIG. 2B having occlusive material 204 in comparison to the intensity of light 112 transmitted across the vessel 200 of FIG. 2A, and the sensor 106 may detect an even lower intensity of light 112 transmitted across the vessel 206 of FIG. 2C having occlusive material 208 in comparison to the intensity of light 112 transmitted across the vessel 202 of FIG. 2B. Thus, in comparison with high vessel patency, low vessel patency can correlate with low intensity of light 112 detected by the sensor 106, and the sensor 106 in turn can convert the lower intensity light 112 into a lower sensor signal.

Referring again to FIG. 1, the wireless transmitter module 108 can be embedded into the housing 102 and can transmit a wireless transmitter signal 116 that can correspond to the intensity of the light 112 detected by the sensor 106. The wireless transmitter signal 116 can be any wireless signal, such as, for example, a radiofrequency (RF) signal, an acoustic signal, or an infrared signal, although such examples are not limiting. In some example implementations, the RF signal can use one or more mobile telecommunication bands, such as 806 to 960 MHz, 1710 to 2025 MHz, 2110 to 2200 MHz, or 2500 to 2690 MHz.

In some example implementations, the wireless transmitter module can transmit a wireless transmitter signal 116 that includes a data representation of the intensity of the light 112 detected by the sensor 106. In other example implementations, the wireless transmitter module 108 can transmit an RF signal having a frequency that corresponds to the intensity of the light 112 detected by the sensor 106. For example, the wireless transmitter module 108 can receive a sensor signal from the sensor 106 (e.g., an electric current from the sensor 106) that is proportional to the intensity of the light 112 detected by the sensor 106. In turn, the wireless transmitter module 108 can transmit, as the wireless transmitter signal 116, an RF signal having a frequency that corresponds to the sensor signal by a predetermined relationship, such as a linear proportionality, a logarithmic proportionality, or the like. More particularly, in some example implementations, the wireless transmitter module 108 can transmit a higher frequency RF signal in response to the sensor signal being high and can transmit a lower frequency RF signal in response to the sensor signal being low. Accordingly, a higher frequency RF wireless transmitter signal can correspond to a higher intensity of light 112 and higher vessel patency (i.e., less vessel occlusion), and a lower frequency RF wireless transmitter signal can correspond to a lower intensity light 112 and lower vessel patency (i.e., greater vessel occlusion). In some example implementations, the RF wireless transmitter signal 116 can be of a range of frequencies that corresponds to a range of vessel patency, such as 0% to 100% patency.

Figure 3:
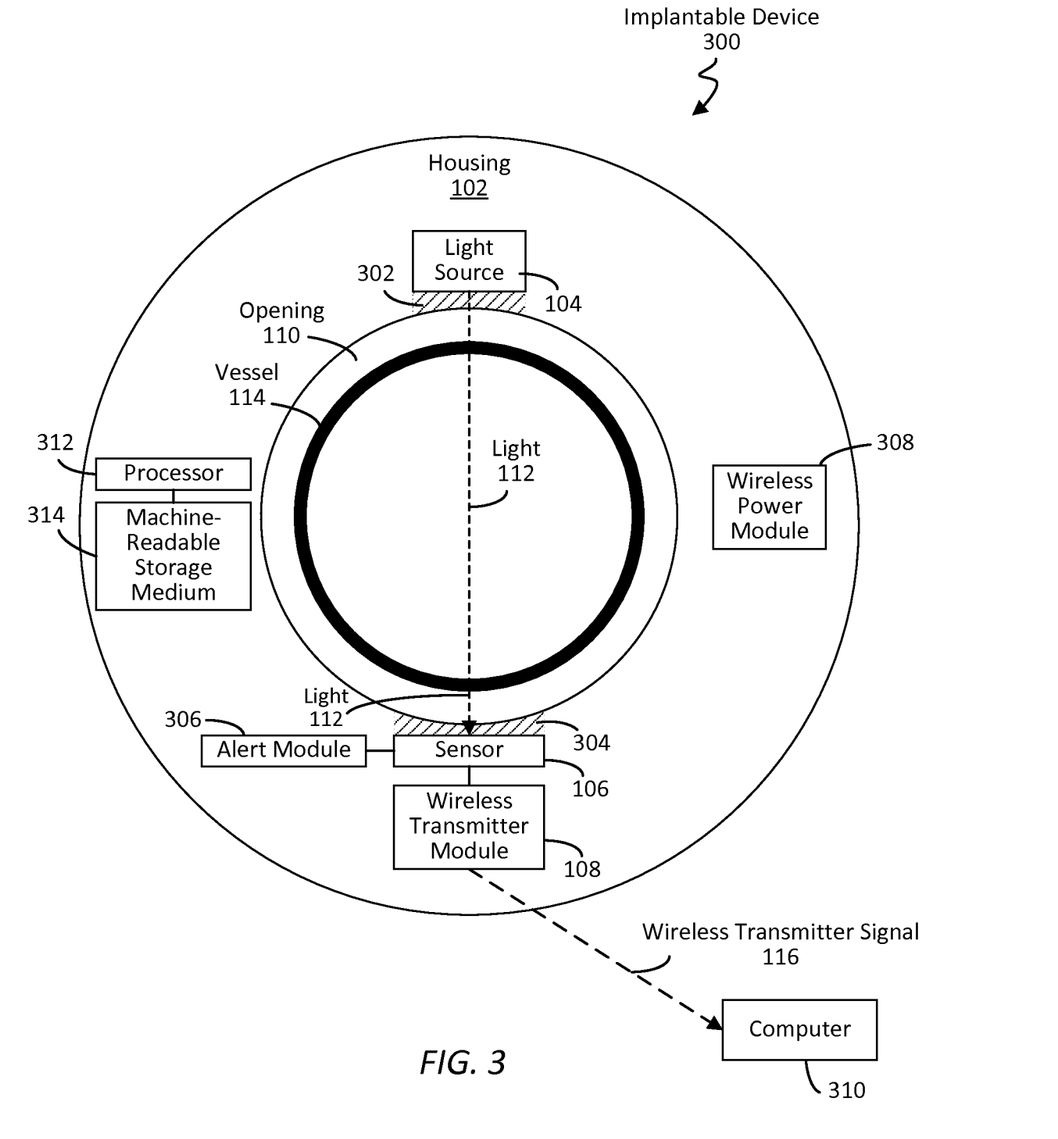
FIG. 3 is a schematic diagram of an implantable device according to another example implementation.

FIG. 3 is a schematic diagram of an implantable device 300 according to another example implementation. As with the implantable device 100 of FIG. 1, the implantable device 300 can include a housing 102, a light source 104, a sensor 106, and a wireless transmitter module 108. The implantable device 300 can also include optically transparent portions of the housing 102 surrounding each of the light source 104 and the sensor 106, an alert module 306, and a wireless power module 308, as will be described further herein below. In some example implementations, the implantable device 300 can also include a processor 312 and a machine-readable storage medium 314.

As described above with reference to FIG. 1, the housing 102 of the implantable device 300 can include an opening 110 for accommodating a vessel 114 of a living body, the light source 104 can be embedded into the housing 102 and can emit light 112, the sensor 106 can be embedded into the housing 102 and can detect light 112 from the light source 104 transmitted across the opening 110 (and thus across a vessel 114 accommodated in the opening 110), and the wireless transmitter module 108 can transmit a wireless transmitter signal 116 that corresponds to an intensity of the light 112 detected by the sensor 106.

In some example implementations, the light source 104 can include electronic circuitry (e.g., a discrete circuit, an integrated circuit, a processor, and the like) and can be controlled by the electronic circuitry to emit light at a pulse frequency of less than or equal to a heart rate associated with the living body (e.g., approximately 60 beats per minute). The pulse frequency of the light can be less than or equal to the heart rate, because the formation of a vessel occlusion typically can occur over a plurality of heart beats. In some example implementations, the light can have a pulse width in the range from one millisecond to five hundred milliseconds.

The processor 312 can include a central processing unit, a multiple processing unit, a microprocessor, an application-specific integrated circuit, a field programmable gate array, and/or other hardware device suitable for retrieval and/or execution of instructions stored in the machine-readable storage medium 314. Additionally or alternatively, the processor 312 can include electronic circuitry for performing the functionality of the implantable device 300 as described herein.

The machine-readable storage medium 314 can be any medium suitable for storing executable instructions, such as a random access memory (RAM), an electrically erasable programmable read-only memory (EEPROM), flash memory devices, and/or other types of volatile memory, non-volatile memory, and storage. In some example implementations, the machine-readable storage medium 314 can be a non-transitory storage medium, where the term "non-transitory" does not encompass transitory propagating signals.

In some example implementations, portions of the housing 102 surrounding each of the light source 104 and the sensor 106 can be optically transparent. For example, the housing 102 can include an optically transparent window 302 adjacent to the light source 104, such that light emitted by the light source 104 passes through the window 302 and then across the opening 110 and the vessel 114 accommodated in the opening 110. Additionally or alternatively, the housing 102 can include an optically transparent window 304 adjacent to the sensor 106, such that light passes from the opening 110 and the vessel 114 accommodated in the opening 110, through the window 304, and to the sensor 106. The optically transparent windows 302 and 304 can be any transparent and biocompatible material, such as glass, sapphire, silicone, poly(methyl methacrylate), other polymers, and the like, although such examples are not limiting.

In some example implementations, the window 302 can serve as an aperture of the light source 104, and, additionally or alternatively, the window 304 can serve as an aperture of the sensor 106. By virtue of the window 302 and/or the window 304 serving as apertures, light can be efficiently directed from the light source 104, across the opening 110 and the vessel 114, and to the sensor 106. Additionally, the amount of other light detected by the sensor 106 that is not from light source 104 (e.g., ambient light, multiply-scattered light, and light from other sources) can be reduced by virtue of the window 302 and/or the window 304 serving as apertures.

The alert module 306 can generate an alert when the intensity of the light 112 detected by the sensor 106 satisfies a predetermined alert criterion associated with reduced patency (i.e., increased occlusion) of the vessel 114 accommodated in the opening 110. The alert module 306 can include, in some example implementations, an audio speaker, a vibrating element, and/or other suitable component(s) that can generate an alert perceivable by the living body.

In some example implementations, the predetermined alert criterion can include the intensity of the light 112 detected by the sensor 106 deviating from a baseline by more than a safety margin. For example, the alert module 306 can receive a sensor signal from the sensor 106 (e.g., an electric current output) that corresponds to the intensity of the light 112 detected by the sensor 106, and the alert module 306 can monitor the sensor signal to detect when the sensor signal, as a proxy for the intensity of light 112, deviates from a baseline sensor signal by more than a safety margin. The baseline sensor signal can be, for example, a sensor signal when the sensor 106 detects light 112 transmitted across a vessel that has high patency, such as the vessel 200 of FIG. 2A described above. In some example implementations, the baseline sensor signal can be a moving average or other like historical measures of the sensor signal. In some example implementations, the safety margin can be a relative difference (e.g., a 10% decrease from the baseline sensor signal) and/or an absolute difference from the baseline sensor signal, and alternatively or additionally, the safety margin can be based on physician expertise and/or medically relevant characteristics of the vessel or of the living body. In some example implementations, the baseline sensor signal and/or the safety margin can be stored in and retrieved from the machine-readable storage medium 314.

When the alert module 306 detects that the sensor signal satisfies the predetermined alert criterion (e.g., the sensor signal calls below the baseline sensor signal by more than 10%), the alert module 306 can generate an audible alert, a vibratory alert, and/or other alert that can be perceived by the living body. In some example implementations, the alert module 306 can generate an alert data signal that can be transmitted by the wireless transmitter module 108 to an electronic device outside of the living body, such as a laptop computer, a desktop computer, a workstation, a tablet computing device, a mobile phone, a server, or the like.

The wireless power module 308 can provide power to at least one component of the implantable device 300, such as the light source 104, the sensor 106, the wireless transmitter module 108, the alert module 306, the processor 312, and/or the machine-readable storage medium 314. The wireless power module 308 can provide power to the at least one component by first receiving power wirelessly from an external power source located outside of the living body (e.g., by electromagnetic induction, electromagnetic radiation, magnetodynamic coupling, and the like), and then supplying the received power to the at least one component by way of electrical connections.

As described above with reference to FIG. 1, the wireless transmitter module 108 can transmit a wireless transmitter signal 116 that can correspond to the intensity of the light 112 detected by the sensor 106. In some example implementations, the wireless transmitter signal 116 can be received by a computer 310, as illustrated in FIG. 3. In some example implementations, the computer 310 can be a laptop computer, a desktop computer, a workstation, a tablet computing device, a mobile phone, a server, or the like. Example implementations of the computer 310 will be described further below with reference to FIGS. 5 and 6.

Figure 4:
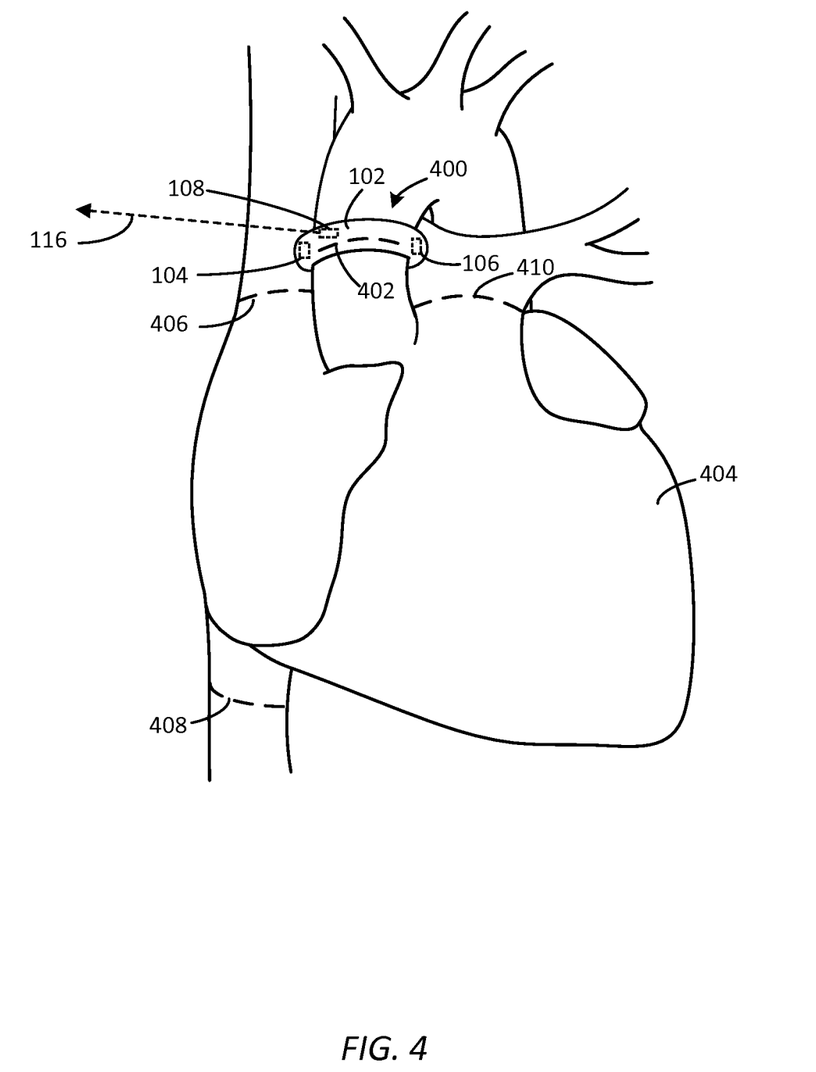
FIG. 4 is an illustration of an example implantable device implanted on a transplanted heart.

FIG. 4 illustrates an implantable device 400, which can be the implantable device 100 of FIG. 1 or the implantable device 300 of FIG. 3. Accordingly, implantable device 400 can include a housing 102 with an opening that accommodates a vessel of a living body, a light source 104 to emit light, a sensor 106 to detect light from the light source 104 transmitted across the vessel, and a wireless transmitter module 108 that transmits a wireless transmitter signal 116 that corresponds to the intensity of the light detected by the sensor 106. The implantable device 400 is depicted as being implanted around an aortic anastomosis 402 of a transplanted heart 404 (that is, the aortic anastomosis 402 is accommodated in an opening of the housing 102 of the implantable device 400). In some example implementations, the implantable device 400 can be useful for detecting formation of a thrombus at the aortic anastomosis 402. The implantable device 400 can also accommodate other vessels or other anastomoses sites of the transplanted heart 404, such as, but not limited to, a superior vena cava anastomosis 406, an inferior vena cava anastomosis 408, and a pulmonary artery anastomosis 410.

Although the implantable device 100 of FIG. 1, the implantable device 300 of FIG. 3, and the implantable device 400 of FIG. 4 are depicted as having an annular shape, it should be understood that other shapes may be utilized. Moreover, although the light source 104 and the sensor 106 are depicted in FIGS. 1, 2A-2C, 3, and 4 to be substantially diametrically opposed, such depiction should be understood to be non-limiting and other configurations can be used to emit light across the opening 110 and the vessel 114 accommodated in the opening 110.

Figure 5:
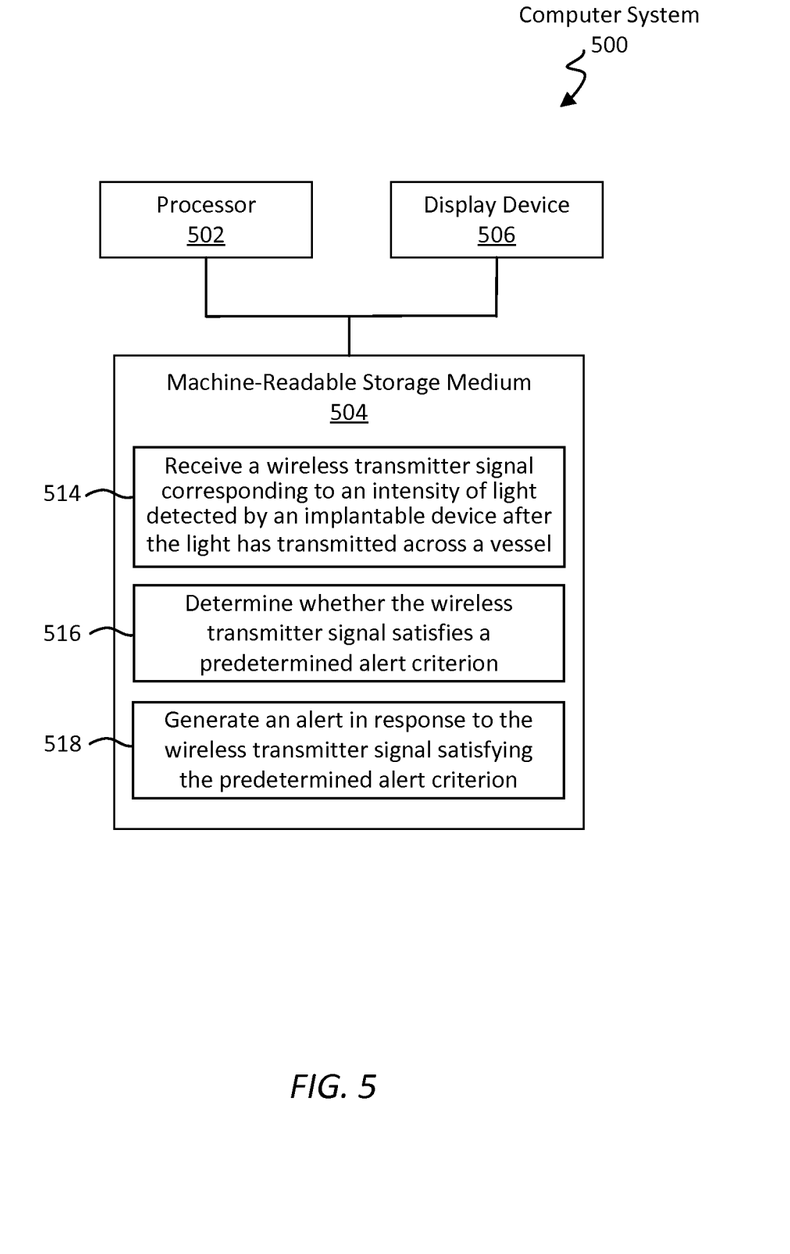
FIG. 5 is a block diagram of a computer that includes a machine-readable storage medium encoded with instructions for generating an alert according to an example implementation.

FIG. 5 is a block diagram of a computer 500 that includes a machine-readable storage medium encoded with instructions for generating an alert according to an example implementation. In some implementations, the computer 500 can serve as or be included in the computer 310 of FIG. 3. In some example implementations, the computer 500 can be a laptop computer, a desktop computer, a workstation, a tablet computing device, a mobile phone, a server, an electronic user device, or the like. The computer system 500 includes a processor 502 coupled to a machine-readable storage medium 504. In some example implementations, the computer system 500 also can include a display device 506.

The processor 502 can include a central processing unit, a multiple processing unit, a microprocessor, an application-specific integrated circuit, a field programmable gate array, and/or other hardware device suitable for retrieval and/or execution of instructions 514, 516, and 518 stored in the machine-readable storage medium 504. Additionally or alternatively, the processor 502 can include electronic circuitry for performing the functionality of instructions 514, 516, and/or 518. The machine-readable storage medium 504 can be any medium suitable for storing executable instructions, such as a random access memory (RAM), an electrically erasable programmable read-only memory (EEPROM), a hard drive, an optical disc, flash memory devices, and the like. In some example implementations, the machine-readable storage medium 504 can be a non-transitory storage medium, where the term "non-transitory" does not encompass transitory propagating signals. As described further herein below, the machine-readable storage medium 504 can be encoded with a set of executable instructions 514, 516, and 518. The display device 506 can include, for example, a monitor, a screen, a light, a speaker, and/or other audio and/or visual devices.

Instructions 514 can receive a wireless transmitter signal transmitted wirelessly by an implantable device (such as the implantable device 100 of FIG. 1 or the implantable device 300 of FIG. 3) implanted around a vessel of a living body. The wireless transmitter signal can correspond to an intensity of light detected by the implantable device after the light has transmitted across the vessel, and the intensity of light can correlate to patency of the vessel. In some example implementations, the RF wireless transmitter signal 116 received by computer 500 can be of a range of frequencies that corresponds to a range of vessel patency, such as 0% to 100% patency. In some example implementations, instructions 514 can receive the wireless transmitter signal by way of the communications interface 510.

In an example implementation, the wireless transmitter signal can be an RF signal having a frequency that corresponds to the intensity of light detected by the implantable device after the light has transmitted across the vessel.

Instructions 516 can determine whether a wireless transmitter signal (e.g., the wireless transmitter signal received by instructions 514) satisfies a predetermined alert criterion associated with reduced patency of the vessel. A wireless transmitter signal that satisfies the predetermined alert criteria can be deemed to indicate reduced vessel patency. In some example implementations, the predetermined alert criterion can include the wireless transmitter signal deviating from the calibration by more than a safety margin. For example, the calibration can be a moving average or other like historical measures of the wireless transmitter signal, and the safety margin can be a percentage difference from the calibration.

For example, in the example implementation described above at instructions 514 where the wireless transmitter signal is an RF signal having a frequency that corresponds to the intensity of light detected by the implantable device after the light has transmitted across the vessel, instructions 516 can identify the frequency of the RF wireless transmitter signal (e.g., by demodulation) and determine whether the identified frequency satisfies a predetermined alert criterion associated with reduced vessel patency, such as a percentage difference (e.g., 10% decrease) in the identified frequency from a calibration (e.g., a moving average or other like historical measures of identified frequencies). (In some example implementations, identifying the frequency can instead be performed as part of instructions 514).

Instructions 518 can generate an alert in response to the wireless transmitter signal satisfying the predetermined alert criterion. In some example implementations, instructions 518 can cause the display device 506 to display a text alert and/or play an audible alert to indicate that a reduced vessel patency condition has been detected.

Figure 6:
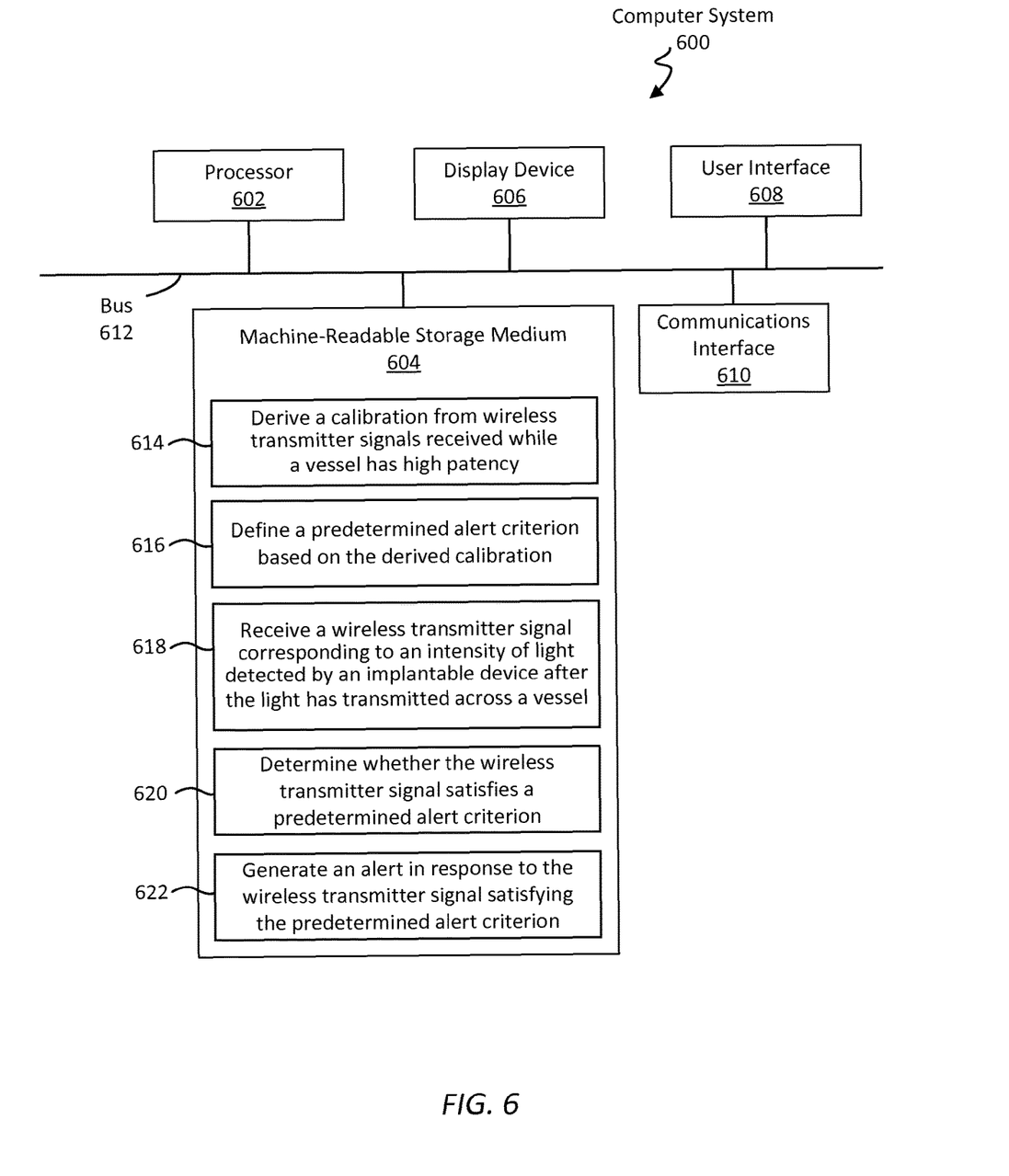
FIG. 6 is a block diagram of a computer that includes a machine-readable storage medium encoded with instructions for generating an alert according to another example implementation.

FIG. 6 is a block diagram of a computer 600 that includes a machine-readable storage medium encoded with instructions for generating an alert according to an example implementation. In some implementations, the computer 600 can serve as or be included in the computer 310 of FIG. 3. In some example implementations, the computer 600 can be a laptop computer, a desktop computer, a workstation, a tablet computing device, a mobile phone, a server, an electronic user device, or the like. The computer system 600 can include a processor 602 coupled to a machine-readable storage medium 604. In some example implementations, the computer 600 can include one or more of a display device 606, a user interface 608, a communications interface 610, and a bus 612. The processor 602, the machine-readable storage medium 604, and the display device 606 can be analogous (e.g., have functions and/or components similar to) to the processor 502, the machine-readable storage medium 504, and the display device 506 of FIG. 5, respectively.

As with the processor 502 of FIG. 5, the processor 602 can include a central processing unit, a multiple processing unit, a microprocessor, an application-specific integrated circuit, a field programmable gate array, and/or other hardware device suitable for retrieval and/or execution of instructions stored in the machine-readable storage medium 604. Additionally or alternatively, the processor 602 can include electronic circuitry for performing the functionality of instructions 614, 616, 618, 620, and/or 622.

As with the machine-readable storage medium 504 of FIG. 5, the machine-readable storage medium 604 can be any medium suitable for storing executable instructions, such as a random access memory (RAM), an electrically erasable programmable read-only memory (EEPROM), a hard drive, an optical disc, flash memory devices, and the like. In some example implementations, the machine-readable storage medium 604 can be a non-transitory storage medium, where the term "non-transitory" does not encompass transitory propagating signals. As described further herein below, the machine-readable storage medium 604 can be encoded with a set of executable instructions 614, 616, 618, 620, and 622.

As with the display device 506 of FIG. 5, the display device 606 can include, for example, a monitor, a screen, a light, a speaker, and/or other audio and/or visual devices. The user interface 608 can include, for example, a keyboard, a mouse, a touch-screen, and/or the like. The communications interface 610 can include any electronic communications technology, such as Ethernet, USB, FireWire, optical fiber, Wi-Fi, Bluetooth, Zigbee, cellular communications, satellite communications, near-field communication, short or long-range radios, and the like. The bus 612 can be used to couple the processor 602, the machine-readable storage medium 604, the display device 606, the user interface 608, and/or the communications interface 610.

Instructions 614 derives a calibration from wireless transmitter signals received from an implantable device (such as the implantable device 100 of FIG. 1 or the implantable device 300 of FIG. 3) while a vessel around which the implantable device is implanted has high patency. In some example implementations, instructions 614 can receive the wireless transmitter signals by way of the communications interface 610. The wireless transmitter signal can correspond to an intensity of light detected by the implantable device after the light has transmitted across the vessel, and the intensity of light can correlate to patency of the vessel. Accordingly, in some example implementations, instructions 614 can derive the calibration by averaging the wireless transmitter signals received while the vessel has high patency. In some example implementations, instructions 614 can store the calibration in the machine-readable storage medium 604.

In some example implementations, instructions 614 can request confirmation by way of the display device 606 and/or the user interface 608 that the vessel has high patency prior to deriving the calibration. For example, a physician may confirm via the display device 606 and/or the user interface 608 that the vessel has high patency after successful implantation of the implantable device around the vessel, or after evaluation by imaging of the vessel (e.g., by angiography, intravenous ultrasound, or the like).

To illustrate an execution of instructions 614, in some example embodiments, the wireless transmitter signal can be an RF signal having a frequency that corresponds to the intensity of light transmitted across a vessel by an implantable device. Instructions 614 can request and receive confirmation by the user interface 606 that the vessel has high patency. After receiving confirmation that the vessel has high patency, instructions 614 can receive RF wireless transmitter signals from the implantable device, can identify the frequencies of the received RF wireless transmitter signals (e.g., by demodulation), and can average the identified frequencies to derive the calibration.

Instructions 616 can define a predetermined alert criterion based on the derived calibration (e.g., the calibration derived by instructions 614). The predetermined alert criterion can be associated with reduced patency of the vessel. In some example implementations, instructions 616 can define the predetermined alert criterion by calculating a safety margin around the derived calibration and defining the predetermined alert criterion as a wireless transmitter signal that is outside the safety margin. For example, the safety margin can be a relative difference (e.g., a 10% difference) and/or an absolute difference from the calibration, and additionally or alternatively, the safety margin can be based on physician expertise and/or medically relevant characteristics of the vessel or of the living body. In some example implementations, instructions 616 can define the predetermined alert criterion by receiving the safety margin as an input from user interface 608. In some example implementations, instructions 616 can store the defined predetermined alert criterion in the machine-readable storage medium 604.

An illustration of the execution of instructions 616 will now be described. As described above in the example illustration of instructions 614, the wireless transmitter signal can be an RF signal having a frequency that corresponds to the intensity of light detected by the implantable device after the light has transmitted across the vessel. More particularly, a higher frequency RF wireless transmitter signal can correspond to a higher intensity of detected light and thus to higher vessel patency (i.e. less vessel occlusion). Similarly, a lower frequency RF wireless transmitter signal can correspond to a lower intensity of detected light and thus to lower vessel patency (i.e., more vessel occlusion). In some example implementations, the RF wireless transmitter signal received by computer 600 can be of a range of frequencies that corresponds to a range of vessel patency, such as 0% to 100% patency. Accordingly, in the foregoing illustration, instructions 616 can define the predetermined alert criterion as wireless transmitter signal frequencies lower than the calibration (e.g., an average of RF wireless transmitter signal frequencies, as described above with reference to instructions 614) by more than a safety margin (e.g., a 10% decrease, although other amounts of relative difference and/or an absolute difference in frequency can be implemented).

Instructions 618, 620, and 622 can be analogous to instructions 514, 516, and 518, respectively. As with instructions 514, instructions 618 can receive wireless transmitter signals transmitted wirelessly by the implantable device that is implanted around a vessel, which can be the same vessel described with respect to instructions 614. Instructions 620 can determine whether a wireless transmitter signal (e.g., the wireless transmitter signal received by instructions 618) satisfies a predetermined alert criterion associated with reduced patency of the vessel. In some example implementations, the predetermined alert criterion can be defined by instructions 616. Accordingly, in the illustration discussed above where a lower RF wireless transmitter signal frequency corresponds to a lower intensity of detected light and thus can correspond to a lower vessel patency, instructions 620 determines whether the frequency of the RF wireless transmitter signal is below the calibration (e.g., as derived by instructions 614) by more than a safety margin (e.g., a 10% decrease). As with instructions 518, instructions 622 can generate an alert in response to the wireless transmitter signal satisfying the predetermined alert criterion.

Figure 7:
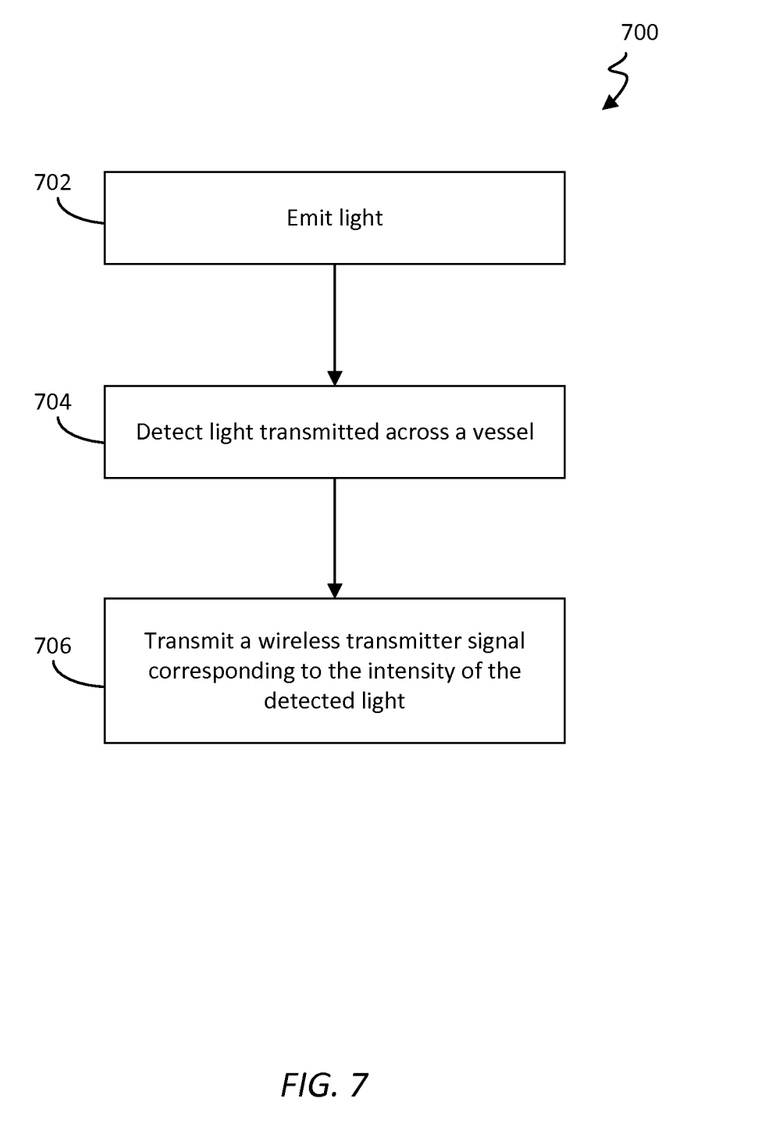
FIG. 7 is a flow diagram of a method for transmitting a signal corresponding to the intensity of light detected by a sensor according to an example implementation.

FIG. 7 is a flow diagram of an example method 700 performed by the device 100 according to an example implementation. Although execution of the method 700 is described below with reference to the device 100 of FIG. 1, it should be understood that execution of some or all of the method 700 can be performed by other suitable devices, such as the device 300 of FIG. 3. The method 700 can be implemented in the form of executable instructions stored on a machine-readable storage medium and/or in the form of electronic circuitry. Prior to starting the method 700, the implantable device 100 can be implanted around the vessel 114 of a living body.

In block 702, the light source 104 embedded into the implantable device 100 implanted around the vessel 114 can emit light. For example, the light source 104 can be an LED that emits light having a wavelength in a range from approximately 400 nm to approximately 700 nm (the visible spectrum). In other example implementations, the light source 104 can emit light having a wavelength in a range from approximately 700 nm to approximately 1400 nm (near infrared light), and more particularly, around 900 nm (e.g. 900 nm±100 nm).

In block 704, the sensor 106 embedded into the implantable device 100 can detect light 112 transmitted across the vessel 114. In other words, in block 704, the sensor 106 can detect light 112 emitted from the light source 104 that has propagated through the vessel 114. For example, the sensor 106 can be a photodetector (e.g., a photodiode) that detects light 112 by converting light 112 arriving at the sensor 106 into a sensor signal, such as an electric current, where the value or amount of the sensor signal is proportional (e.g., by linear proportionality, logarithmic proportionality, or the like) to the intensity of the light 112 arriving at the sensor 106.

The intensity of light 112 detected by sensor 106 in block 704 can correlate to (i.e., be affected by) patency of the vessel 114. For example, as described above with reference to FIGS. 2A-2C, light 112 transmitted across an unoccluded vessel (e.g., the vessel 200 of FIG. 2A) and detected by sensor 106 in block 704 can have a higher intensity than light 112 transmitted across a vessel with diminished patency (e.g., the vessel 202 of FIG. 2B or the vessel 206 of FIG. 2C).

In block 706, the wireless transmitter module 108 embedded into the implantable device 100 can transmit a wireless transmitter signal 116 that corresponds to the intensity of the light 112 detected by the sensor 106 in block 704.

Figure 8:
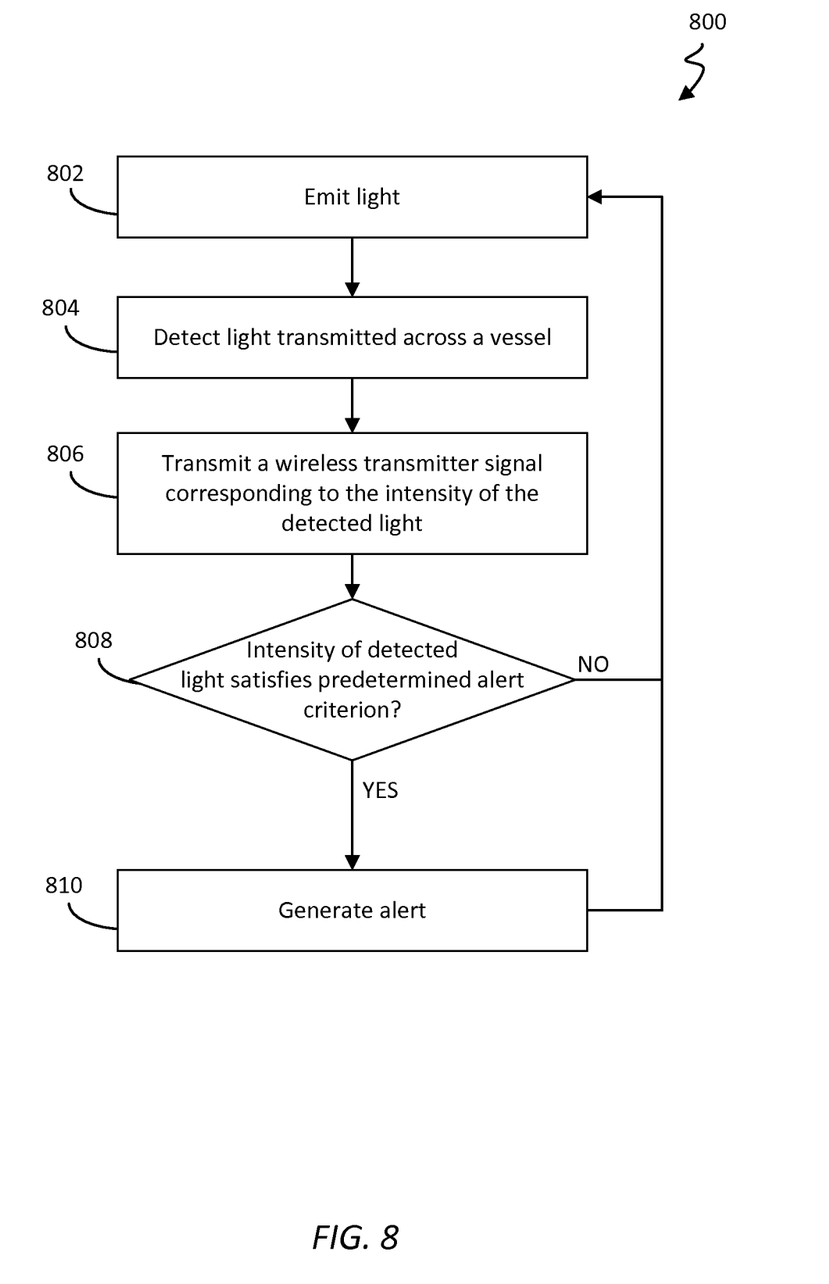
FIG. 8 is a flow diagram of a method for transmitting a signal corresponding to the intensity of light detected by a sensor according to another example implementation.

FIG. 8 is a flow diagram of an example method 800 performed by a device 300 according to an example implementation. Although execution of the method 800 is described below with reference to the device 300 of FIG. 3, it should be understood that execution of some or all of the method 800 can be performed by other suitable devices, such as the device 100 of FIG. 1. The method 800 can be implemented in the form of executable instructions stored on a machine-readable storage medium and/or in the form of electronic circuitry. As with the method 700 of FIG. 7, the implantable device 300 can be implanted around the vessel 114 of the living body prior to starting the method 800 of FIG. 8.

Blocks 802, 804, and 806 of FIG. 8 can be analogous in many respects to blocks 702, 704, and 706 of FIG. 7, respectively. As with block 702, in block 802, the light source 104 embedded into the implantable device 300 implanted around the vessel 114 can emit light. In some example implementations, the light source 104 can emit light in block 802 at a pulse frequency of less than or equal to a heart rate associated with the living body (e.g., approximately 60 beats per minute). The pulse frequency can be less than or equal to the heart rate because the formation of a vessel occlusion typically occurs over a plurality of heart beats. In some example implementations, the pulse of light can have a pulse width in the range from one millisecond to five hundred milliseconds.

As with block 704, in block 804, the sensor 106 embedded into the implantable device 100 can detect the light 112 emitted across the vessel 114. For example, the sensor 106 can convert light 112 into a sensor signal, such as an electric current.

As with block 706, in block 806, the wireless transmitter module 108 embedded into the implantable device 100 can transmit a wireless transmitter signal 116 that corresponds to the intensity of the light 112 detected by the sensor 106 in block 804.

In some example implementations, the wireless transmitter signal 116 can be a data representation of the intensity of the light 112 detected by the sensor 106. In some example implementations, the wireless transmitter module 108 transmits, as wireless transmitter signal 116, an RF signal having a frequency that corresponds to the intensity of the light 112 detected by the sensor 106 in block 804. For example, the frequency of the transmitted RF signal can be proportional (e.g., by a predetermined relationship, such as, linear proportionality, logarithmic proportionality, or the like) to the sensor signal (e.g., the electric current output of a photodetector sensor 106); that is, the wireless transmitter module 108 can transmit a high frequency RF signal in response to the sensor signal being high and can transmit a lower frequency RF signal in response to the sensor signal being low. In some example implementations, the RF wireless transmitter signal 116 can be of a range of frequencies that corresponds to a range of vessel patency, such as 0% to 100% patency.

In block 808, an alert module 306 determines whether the intensity of light 112 detected by the sensor 106 in block 804 satisfies a predetermined alert criterion associated with reduced patency of the vessel 114.

In some example implementations, the alert module 306 performs block 808 by receiving from the sensor 106 a sensor signal that corresponds to the intensity of the light 112 detected by the sensor 106 in block 804, and monitoring the sensor signal to detect when the sensor signal satisfies a predetermined alert criterion. In some example implementations, the sensor signal satisfies the predetermined alert criterion when the sensor signal deviates from a baseline sensor signal by more than a safety margin. The baseline sensor signal can be, for example, a sensor signal corresponding to the intensity of light 112 passing through the vessel 114 when the vessel 114 is deemed to have high patency. In some example implementations, the baseline sensor signal can be a moving average or other like historical measures of the sensor signal. In some example implementations, the safety margin can be a relative difference (e.g., a 10% difference) and/or an absolute difference from the baseline sensor signal, and in some example implementations, the safety margin can be based on physician expertise and/or medically relevant characteristics of the vessel or of the living body. In some example implementations, the baseline sensor signal and/or the safety margin can be stored in and retrieved from the machine-readable storage medium 314.

If block 808 determines that the intensity of light 112 detected by the sensor 106 satisfies the predetermined alert criterion ("YES" at block 808), the method 800 proceeds to block 810 and generates an alert. In some example implementations, the alert module 306 can generate an audible alert, a vibratory alert, and/or other alert that can be perceived by the living body in which the implantable device 300 is implanted. In other example implementations, the alert module 306 can generate an alert data signal that can be transmitted by the wireless transmitter module 108 to an electronic device outside of the living body, such as a laptop computer, a desktop computer, a workstation, a tablet computing device, a mobile phone, a server, or the like.

The method 800 can proceed back to block 802 after completing block 810. The method 800 can also proceed back to block 802 after completing block 808 if the intensity of detected light 112 does not satisfy the predetermined alert criterion ("NO" at block 808). By virtue of returning to block 802, the method 800 can continuously monitor the patency of the vessel 114.

Figure 9:
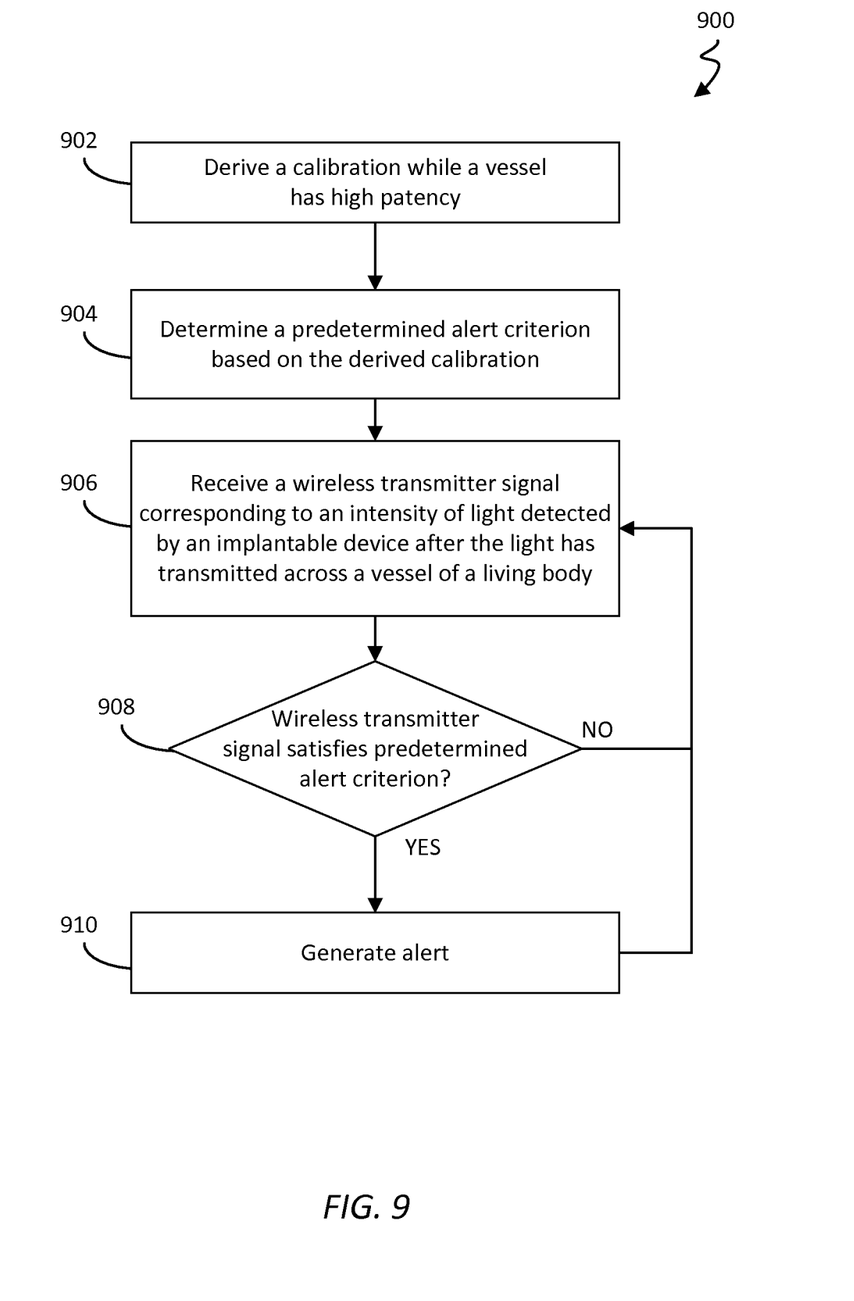
FIG. 9 is a flow diagram of a method for generating an alert according to an example implementation.

FIG. 9 is a flow diagram of an example method 900 performed by a computer 600 according to an example implementation. Although execution of the method 900 is described below with reference to the computer 600 of FIG. 6, it should be understood that execution of some or all of the method 900 can be performed by other suitable devices, such as the computer 500 of FIG. 5. The method 900 can be implemented in the form of executable instructions stored on a machine-readable storage medium 604 and/or in the form of electronic circuitry.

In block 902, the processor 602 can derive a calibration from wireless transmitter signals received from an implantable device (such as the implantable device 100 of FIG. 1 or the implantable device 300 of FIG. 3) while a vessel around which the implantable device is implanted has high patency. In some example implementations, the processor 602 can receive the wireless transmitter signals by way of the communications interface 610. The wireless transmitter signal can be an RF signal that corresponds to an intensity of light detected by the implantable device after the light has transmitted across the vessel (e.g., the wireless transmitter signal 116 transmitted in block 706 of FIG. 7 or block 806 of FIG. 8), and the intensity of light can correlate to patency of the vessel. Accordingly, in some example implementations, a calibration can be derived by averaging the wireless transmitter signals received while the vessel has high patency. In some example implementations, the processor 602 can store the calibration in the machine-readable storage medium 604.

In some example implementations, as part of block 902, the processor 602 can request confirmation by way of the display device 606 and/or the user interface 608 that the vessel has high patency prior to deriving the calibration. For example, a physician may confirm via the display device 606 and/or the user interface 608 that the vessel has high patency after successful implantation of the implantable device around the vessel, or after evaluation by imaging of the vessel (e.g., by angiography, intravenous ultrasound, or the like). In other example implementations, the processor 602 can assume that the vessel has high patency for a period of time following the start of the method 900, which can follow substantially soon after successful implantation of the implantable device around the vessel (i.e., while the patient is under anticoagulation treatment) or after the implantable device is powered on for the first time.

In some example implementations, the wireless transmitter signal can be an RF signal having a frequency that corresponds to the intensity of light detected by the implantable device after the light has transmitted across the vessel. The processor 602 can request and receive confirmation by the user interface 606 that the vessel has high patency. Then, the processor 602 can receive RF wireless transmitter signals from an implantable device, can identify the frequencies of the received RF wireless transmitter signals (e.g., by demodulation), and can average the identified frequencies to derive the calibration.

In block 904, the processor 602 can define a predetermined alert criterion based on the calibration derived in block 902. The predetermined alert criterion can be associated with state of reduced patency of the vessel. In some example implementations, the processor 602 can define the predetermined alert criterion by calculating a safety margin around the derived calibration and defining the predetermined alert criterion as a wireless transmitter signal that is outside the safety margin. For example the safety margin can be a relative difference (e.g., a 10% difference) and/or an absolute difference from the calibration, and in some example implementations, the safety margin can be based on physician expertise and/or medically relevant characteristics of the vessel or of the living body. In some example implementations, the processor 602 can define the predetermined alert criterion by receiving the safety margin as an input from user interface 608. In some example implementations, the processor 602 can store the defined predetermined alert criterion in the machine-readable storage medium 604.

For example, in the example implementations where the wireless transmitter signal can be an RF signal having a frequency that corresponds to the intensity of light detected by the implantable device after the light has transmitted across the vessel, a higher frequency of the RF wireless transmitter signal can correspond to a higher intensity of detected light and thus to higher vessel patency (i.e., less vessel occlusion). Similarly, a lower frequency RF wireless transmitter signal can correspond to a lower intensity of detected light and thus to lower vessel patency (i.e., more vessel occlusion). In some example implementations, the RF wireless transmitter signal received by computer 600 can be of a range of frequencies that corresponds to a range of vessel patency, such as 0% to 100% patency. So as to detect reductions in vessel patency, the predetermined alert criterion can be defined as RF wireless transmitter signal frequencies that are lower than the calibration (e.g., an average of the RF wireless transmitter signal frequencies received while the vessel has high patency, as described above with reference to block 902) by more than a safety margin (e.g., a 10% decrease, although other amounts of relative difference and/or an absolute difference in frequency can be implemented).

In some example implementations, blocks 902 and 904 can be useful for calibrating the computer 600 after the implantable device has been implanted around the vessel or at another time when a calibration is deemed necessary (e.g., by a physician).

In block 906, the processor 602 can receive a wireless transmitter signal transmitted wirelessly by an implantable device (such as the implantable device 100 of FIG. 1 or the implantable device 300 of FIG. 3) implanted around a vessel of a living body, which can be the same vessel described with respect to block 902. In some example implementations, the processor 602 can receive the wireless transmitter signal by way of the communications interface 610. The wireless transmitter signal can correspond to an intensity of light detected by the implantable device after the light has transmitted across the vessel, and the intensity of light can correlate to patency of the vessel.

In some example implementations, the wireless transmitter signal received in block 906 can be an RF signal having a frequency that corresponds to the intensity of the light detected by the implantable device after the light has transmitted across the vessel. For example, the wireless transmitter signal can be the wireless transmitter signal 116 transmitted in block 706 of FIG. 7 or block 806 of FIG. 8.

In block 908, the processor 602 can determine whether the wireless transmitter signal received in block 906 satisfies a predetermined alert criterion associated with reduced patency of the vessel. In some example implementations, a wireless transmitter signal that satisfies the predetermined alert criterion can be deemed to indicate reduced vessel patency. In some example implementations, the predetermined alert criterion can include the wireless transmitter signal (e.g., the wireless transmitter signal received at block 906) deviating from the calibration by more than a safety margin. For example, the calibration can be a moving average or other like historical measures of the wireless transmitter signal, and the safety margin can be a percentage difference from the calibration.

For example, in the example implementations where the wireless transmitter signal can be an RF signal having a frequency that corresponds to the intensity of light detected by the implantable device after the light has transmitted across the vessel, the processor 602 can perform block 908 by identifying the frequency of the wireless transmitter signal received in block 906 (e.g., by demodulation) and determining whether the identified frequency satisfies the predetermined alert criterion associated with reduced vessel patency, such as a percentage difference (e.g., a 10% decrease) in the identified frequency from a calibration (e.g., a moving average or other like historical measures of identified frequencies). (In some example implementations, the processor 602 can instead identify the frequency as part of block 906.) If the identified frequency deviates from the calibration by more than the safety margin (e.g., more than a 10% decrease, in some example implementations), the wireless transmitter signal is deemed (i.e., determined) to satisfy the predetermined alert criterion associated with reduced patency of the vessel by processor 602 in block 908.

Block 910 can be performed if the processor 602 determines, in block 908, that the wireless transmitter signal received in block 906 satisfies the predetermined alert criterion ("YES" at block 908). In block 910, the processor 602 can generate an alert in response to the wireless transmitter signal satisfying the predetermined alert criterion. In some example implementations, the processor 602 can cause the display device 606 to display a text alert and/or play an audible alert to indicate that a reduced vessel patency condition has been detected.

The method 900 can proceed back to block 906 after completing block 910. The method 900 also can proceed back to block 906 after completing block 908 if the wireless transmitter signal received in block 906 does not satisfy the predetermined alert criterion ("NO" at block 908). By virtue of returning to block 906, the method 900 can continuously monitor the patency of the vessel.

Figure 10:
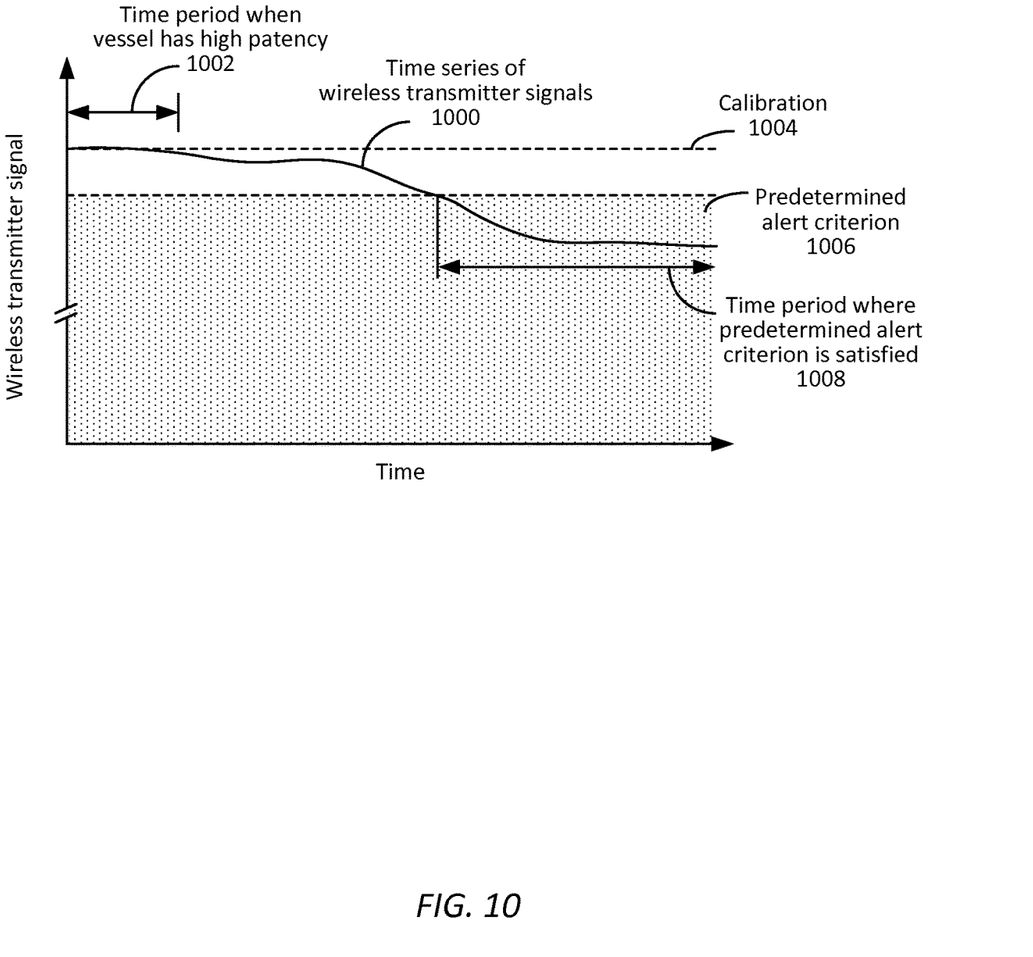
FIG. 10 is an example illustration of the method of FIG. 9.

The method 900, as performed by the computer 600, will now be illustrated with reference to FIG. 10. FIG. 10 illustrates an example time series of wireless transmitter signals 1000 received by the processor 602. During a period of time 1002 when the vessel is deemed to have high patency, the processor 602 can execute block 902 to derive a calibration 1004, which can be the average of the frequencies of wireless transmitter signals during the time period 1002. After the calibration 1004 has been derived, the processor 602 can execute block 904 to define a predetermined alert criterion 1006, such as wireless transmitter signals lower than the calibration 1004 by more than a safety margin (e.g., more than 10% below the calibration 1004). After the predetermined alert criterion 1006 has been defined, the processor 602 can execute block 906 to receive wireless transmitter signals, and the processor 602 can execute block 908 to determine whether the wireless transmitter signals satisfy the predetermined alert criterion 1006. For example, the processor 602 can determine that the wireless transmitter signals 1000 received during the time period 1008 satisfies the predetermined alert criterion 1006 (that is, the wireless transmitter signals fall below the calibration 1004 by more than the safety margin), and the processor 602 then generates an alert by executing block 910.

In view of the foregoing description, it can be appreciated that the patency of a vessel can be monitored remotely and conveniently using an implantable device, without resorting to blood draws or catheter-based imaging. In particular, by virtue of the implantable device described herein, physicians may be able to detect and reduce surgical complications related to vessel occlusion, such as thrombosis at an anastomosis of a heart transplant. Moreover, by virtue of the use of light to monitor vessel patency, the implantable device may be safely utilized for chronic, long-term monitoring of vessel patency.

In the foregoing description, numerous details are set forth to provide an understanding of the subject disclosed herein. However, implementation may be practiced without some or all of these details. Other implementations may include modifications and variations from the details discussed above. It is intended that the following claims cover such modifications and variations.

We claim:

1. An implantable device for monitoring vessel patency comprising:
 a housing that includes an opening for accommodating a vessel of a living body;
 first and second windows in the housing, the second window being diametrically opposed from the first window;
 a light source, embedded into the housing and behind the first window such that light emanating from the light source passes through the first window, including electronic circuitry that is configured to control the light source to emit light at a pulse frequency of less than or equal to a heart rate associated with the living body;
 a sensor, embedded into the housing diametrically opposed from the light source and behind the second window such that light emanating from the light source passes through the first window, to detect light transmitted from the light source across the opening such that the sensor detects the light passed through the vessel, wherein the second window in combination with the housing limits light from other light sources reaching the sensor, and wherein an intensity of the detected light by the sensor correlates to patency of the vessel accommodated in the opening;
 a processor, the processor programmed to:
  acquire a baseline sensor signal corresponding to an intensity of light;
  select, from a range of available radio frequencies, a radio frequency based on the intensity of the detected light, and
  determine that the intensity of the detected light deviates from the baseline sensor signal by more than a safety margin; and
 a wireless transmitter, embedded into the housing, to transmit an alert data signal at the selected radio frequency in response to the determined deviation of the intensity of the detected light from the baseline sensor signal being more than the safety margin.

2. The implantable device of claim 1, wherein
 the light is near infrared light, and
 portions of the housing surrounding each of the light source and the sensor are optically transparent.

3. The implantable device of claim 1, further comprising a wireless power source that provides power to at least one of the light source, the sensor, and the wireless transmitter.

4. The implantable device of claim 1, further comprising an alert module including at least one of an audio speaker configured to generate an audible alert or a vibrating element configured to generate a vibratory alert.

5. The implantable device of claim 1, wherein the light emitted has a wavelength in a range from 806 nm to 939 nm.

6. The implantable device of claim 1, wherein the housing is defined by a uniform ring-shaped exterior that lacks an opening along the exterior.

* * * * *